US012564400B2

(12) United States Patent
Perryman

(10) Patent No.: US 12,564,400 B2
(45) Date of Patent: Mar. 3, 2026

(54) STAPLE INSERTER WITH PUSH-BUTTON RELEASE

(71) Applicant: Tyber Medical LLC, Bethlehem, PA (US)

(72) Inventor: John Abraham Perryman, Columbia, TN (US)

(73) Assignee: Tyber Medical LLC, Bethlehem, PA (US)

( * ) Notice: Subject to any disclaimer, the term of this patent is extended or adjusted under 35 U.S.C. 154(b) by 0 days.

(21) Appl. No.: 19/027,255

(22) Filed: Jan. 17, 2025

(65) Prior Publication Data

US 2025/0241639 A1     Jul. 31, 2025

Related U.S. Application Data

(60) Provisional application No. 63/625,308, filed on Jan. 26, 2024.

(51) Int. Cl.
*A61B 17/068* (2006.01)
*A61B 17/00* (2006.01)
*A61B 90/00* (2016.01)

(52) U.S. Cl.
CPC .......... *A61B 17/0682* (2013.01); *A61B 90/03* (2016.02); *A61B 2017/00367* (2013.01); *A61B 2090/034* (2016.02)

(58) Field of Classification Search
CPC ................ A61B 17/0682; A61B 90/03; A61B 2090/034; A61B 2017/00367
See application file for complete search history.

(56) References Cited

U.S. PATENT DOCUMENTS

2019/0142415 A1 * 5/2019 Valiani ................. A61B 17/068
                                                                                    227/177.1
2024/0315996 A1 * 9/2024 Torne ....................... A61K 9/10

* cited by examiner

*Primary Examiner* — Michelle Lopez
(74) *Attorney, Agent, or Firm* — Joseph E. Maenner; Maenner & Associates, LLC

(57) ABSTRACT

A staple inserter provides a member having a proximal end, a distal end, and an elongate body extending between the proximal end and the distal end. The body has a cavity at the distal end. A slider is slidingly disposed on the body and includes a distal lip covering the cavity when in a locked position. The lip exposes the cavity when in an unlocked position. A staple is retained in the cavity.

16 Claims, 3 Drawing Sheets

STAPLE INSERTER WITH PUSH-BUTTON RELEASE

BACKGROUND OF THE INVENTION

Field of the Invention

The invention relates to a medical staple inserter with a push-button to release a slide covering the staple, thereby enabling the staple to be removed from the inserter.

Description of the Related Art

Medical staples are often used to close wounds or to secure bone fragments to each other.

It would be beneficial to provide a staple inserter that can be selectively activated to release a staple.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a staple inserter providing a member having a proximal end, a distal end, and an elongate body extending between the proximal end and the distal end. The body has a cavity at the distal end. A slider is slidingly disposed on the body and includes a distal lip covering the cavity when in a locked position. The lip exposes the cavity when in an unlocked position. A staple is retained in the cavity.

In an alternative embodiment, the present invention provides a staple inserter comprising a member having a proximal end, a distal end, and an elongate body extending between the proximal end and the distal end. The body has a cavity at the distal end. A slider is slidingly disposed on the body. The slider includes a distal lip covering the cavity when the slider is in a locked position and exposing the cavity when the slider is in an unlocked position. A button is located proximal of the slider along the body and, when the slider is in an engaged position, the button prevents the slider from sliding proximally.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION

Figure 1:
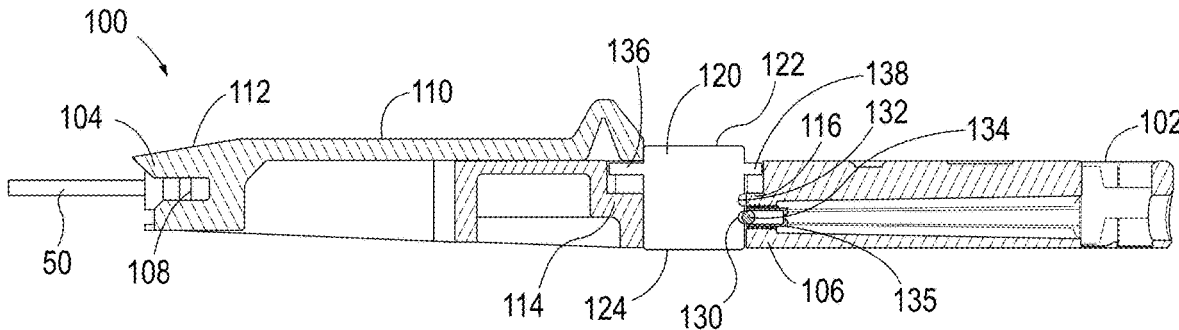
FIG. 1 is aside elevational view, in section, of a staple inserter with release button in an engaged position according to an exemplary embodiment of the present invention.

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "proximal" is a direction closer to the user of the inventive device and the term "distal" is a direction farther from the user of the inventive device.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

The word "about" is used herein to include a value of +/−10 percent of the numerical value modified by the word "about" and the word "generally" is used herein to mean "without regard to particulars or exceptions."

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Referring to the Figures, a staple inserter 100 according to an exemplary embodiment of the present invention is shown. While the present invention is used with a staple inserter, those skilled in the art will recognize that the present invention can be used with other devices to releasably lock/unlock a sliding mechanism.

Inserter 100 includes a proximal end 102, a distal end 104, and an elongate body 106 extending between proximal end 102 and distal end 104. Body 106 extends along a longitudinal axis 101. A staple 50 is retained at distal end 104 in a cavity 108. Staple comprises legs 52 that extend parallel to the longitudinal axis 101.

A slider 110 is slidingly disposed on body 106. Slider 110 includes a distal lip 112 that covers cavity 108 when in a locked position, as shown in FIG. 1, so that staple 50 cannot be removed from inserter 100.

A button 120 is located proximal of slider 110 along body 106. Button 120 is movable in a direction transverse to longitudinal axis 101. When button 120 is in an engaged position, as shown in FIG. 1, button 120 prevents slider 110 from sliding proximally.

Figure 2:
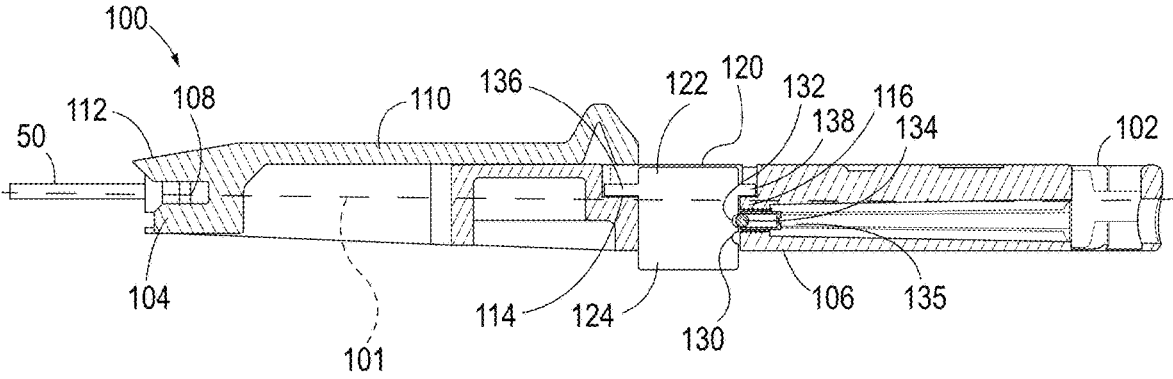
FIG. 2 is a side elevational view, in section, of the staple inserter of FIG. 1, with the button in a release position.

A top surface 122 of button 120 extends above body 106 in the engaged position and can be depressed to be level with body 106, as shown in FIG. 2, in a release position. A bottom surface 124 of button 120 is level with body 106 in the engaged position and, when button 120 is depressed into the release position, as shown in FIG. 2, bottom surface 124 extends below body 106 so that button 120 can be ultimately pressed upward back to the engaged position, if desired.

Button 120 includes a pair of proximal detents 130, 132 formed therein. Detents 130, 132 alternatively engage a spring-biased ball 134 mounted in body 106. Ball 134 is sized to fit into either detent 130 or detent 132. Ball 134 is supported by a threaded member 135 that is threaded into body 106 from proximal end 102. Threaded member 135 houses a biasing member, such as a spring 137, that biases ball 134 in a distal direction.

Figure 3:
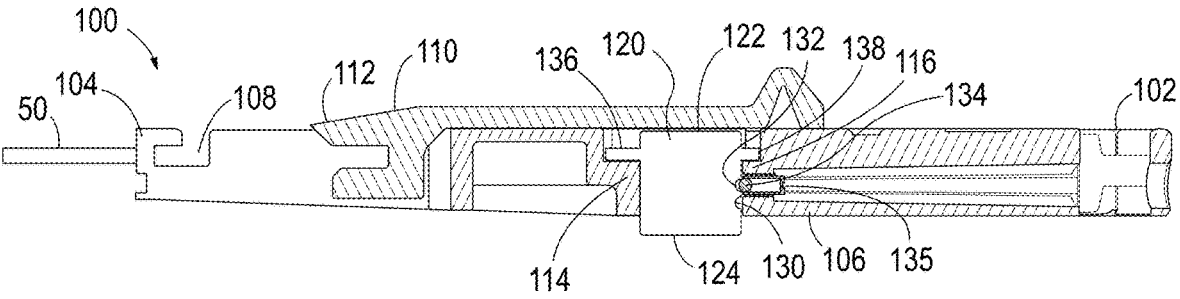
FIG. 3 is a side elevational view, in section, of the inserter of FIG. 1 with the slider slid in a proximal direction.

When button 120 is in the engaged position, as shown in FIG. 1, ball 134 is in detent 130. When button 120 is depressed to the release position, as shown in FIGS. 2 and 3, ball 134 is forced out of detent 130 and biases into detent 132. This allows button 120 to remain depressed in the release position without having to maintain pressure on button 120.

Button 120 also includes a distal ledge 136 and a proximal ledge 138. Ledges 136, 138 engage vertical stops 114, 116, respectively, that engage their respective ledges 136, 138 when button 120 is in the release position to stop the downward travel of button 120.

With button 120 depressed to the release position as shown in FIG. 2, slider 110 can be slid distally along body 106 from the position shown in FIG. 2 to the position shown in FIG. 3, thereby exposing cavity 108 and allowing staple 50 to be released from inserter 100.

It will be further understood that various changes in the details, materials, and arrangements of the parts which have been described and illustrated in order to explain the nature of this invention may be made by those skilled in the art without departing from the scope of the invention as expressed in the following claims.

I claim:

1. A staple inserter comprising:

a member having a proximal end, a distal end, and an elongate body extending between the proximal end and the distal end, the body having a cavity at the distal end;

a slider slidingly disposed on the body, the slider including a distal lip covering the cavity when in a locked position and exposing the cavity when in an unlocked position;

a staple retained in the cavity, and a button located proximal of the slider along the body and, when the button is in engagement with the slider the engagement locks and prevents the slider from sliding proximally.

2. The staple inserter according to claim 1, wherein the button has a top surface such that the top surface extends above the body in the engaged position and is depressible to be level with the body in a release position.

3. The staple inserter according to claim 2, wherein the button has a bottom surface such that the bottom surface is level with body in the engaged position and, when the button is depressed into the release position, the bottom surface extends below the body.

4. The staple inserter according to claim 1, wherein the button has a pair of proximal detents formed therein.

5. The staple inserter according to claim 4, wherein the proximal detents alternatively engage a spring-biased ball mounted in the body.

6. The staple inserter according to claim 5, wherein the ball is sized to fit into either detent of the pair of proximal detents.

7. The staple inserter according to claim 6, wherein, when the button is in the engaged position, the ball is in a first of the pair of proximal detents.

8. The staple inserter according to claim 7, wherein, when the button is depressed to the release position, the ball is forced out of the first of the pair of proximal detents and biases into the second of the pair of proximal detents.

9. The staple inserter according to claim 8, wherein, when the button is depressed to the release position, the slider is slidable distally along the body, thereby exposing the cavity and allowing the staple to be released from the inserter.

10. The staple inserter according to claim 5, wherein the ball is supported by a threaded member inserted into the proximal end of the body.

11. The staple inserter according to claim 10, wherein the threaded member houses a biasing member configured to bias the ball in a distal direction.

12. The staple inserter according to claim 1, wherein the button includes a distal ledge and a proximal ledge.

13. The staple inserter according to claim 12, wherein the body includes a vertical stop on either side of the button such that the distal ledge and the proximal ledge each engages one of the vertical stops when the button is in the release position.

14. A staple inserter comprising:

a member having a proximal end, a distal end, and an elongate body extending between the proximal end and the distal end, the body having a cavity at the distal end;

a slider slidingly disposed on the body, the slider including a distal lip covering the cavity when the slider is in a locked position and exposing the cavity when the slider is in an unlocked position; and a button located proximal of the slider along the body and, when the slider is is engaged with the button, the button prevents the slider from sliding proximally.

15. The staple inserter according to claim 14, wherein the body extends along a longitudinal axis and wherein the button is movable in a direction transverse to the longitudinal axis.

16. The staple inserter according to claim 14, further comprising a staple inserted into the cavity, wherein the staple comprises legs, wherein the legs extend parallel to the longitudinal axis.

* * * * *